US007981635B2

(12) United States Patent
Zocher et al.

(10) Patent No.: US 7,981,635 B2
(45) Date of Patent: Jul. 19, 2011

(54) CLEAVAGE OF PRECURSORS OF INSULINS BY A VARIANT OF TRYPSIN

(75) Inventors: Frank Zocher, Frankfurt am Main (DE); Christoph Hoh, Frankfurt am Main (DE); Rainer Mueller, Penzberg (DE); Erhard Kopetzki, Penzberg (DE); Frank Geipel, Penzberg (DE); Stephan Glaser, Seeshaupt (DE)

(73) Assignees: Sanofi-Aventis Deutschland GmbH (DE); Roche Diagnostics Operations, Inc., Indianapolis, IN (US)

( * ) Notice: Subject to any disclaimer, the term of this patent is extended or adjusted under 35 U.S.C. 154(b) by 127 days.

(21) Appl. No.: 12/063,313

(22) PCT Filed: Aug. 26, 2006

(86) PCT No.: PCT/EP2006/008380
§ 371 (c)(1),
(2), (4) Date: Mar. 17, 2010

(87) PCT Pub. No.: WO2007/031187
PCT Pub. Date: Mar. 22, 2007

(65) Prior Publication Data
US 2010/0196953 A1 Aug. 5, 2010

(30) Foreign Application Priority Data

Sep. 14, 2005 (EP) .................... 05077086

(51) Int. Cl.
*C12P 21/06* (2006.01)
*C12N 9/76* (2006.01)
(52) U.S. Cl. ...................... 435/68.1; 435/213
(58) Field of Classification Search .................. None
See application file for complete search history.

(56) References Cited

U.S. PATENT DOCUMENTS

| | | | |
|---|---|---|---|
| 4,683,293 A | 7/1987 | Craig |
| 4,808,537 A | 2/1989 | Stroman et al. |
| 4,812,405 A | 3/1989 | Lair et al. |
| 4,818,700 A | 4/1989 | Cregg et al. |
| 4,837,148 A | 6/1989 | Cregg |
| 4,855,231 A | 8/1989 | Stroman et al. |
| 4,857,467 A | 8/1989 | Sreekrishna et al. |
| 4,870,008 A | 9/1989 | Brake |
| 4,879,231 A | 11/1989 | Stroman et al. |
| 4,882,279 A | 11/1989 | Cregg |
| 4,885,242 A | 12/1989 | Cregg |
| 4,895,800 A | 1/1990 | Tschopp |
| 4,929,555 A | 5/1990 | Cregg et al. |
| 5,002,876 A | 3/1991 | Sreekrishna et al. |
| 5,004,688 A | 4/1991 | Craig et al. |
| 5,032,516 A | 7/1991 | Cregg |
| 5,122,465 A | 6/1992 | Cregg et al. |
| 5,135,868 A | 8/1992 | Cregg |
| 5,166,329 A | 11/1992 | Cregg |
| 5,324,639 A | 6/1994 | Brierly |
| 5,618,676 A | 4/1997 | Hitzeman et al. |
| 5,854,018 A | 12/1998 | Hitzeman et al. |
| 5,856,123 A | 1/1999 | Hitzman et al. |
| 5,919,651 A | 7/1999 | Hitzman et al. |
| 6,852,513 B1* | 2/2005 | Bongs et al. ........... 435/69.4 |
| 2004/0203095 A1* | 10/2004 | Muller et al. ........... 435/69.1 |

FOREIGN PATENT DOCUMENTS

| | | |
|---|---|---|
| DE | 19821866 | 11/1999 |
| EP | 0055945 | 7/1982 |
| EP | 0116201 | 8/1984 |
| EP | 0214826 | 3/1987 |
| EP | 0375437 | 6/1990 |
| EP | 0678522 | 10/1995 |
| WO | 89/10937 | 11/1989 |
| WO | 00/56903 | 9/2000 |
| WO | 2004/029202 | 4/2004 |

OTHER PUBLICATIONS

Calmels et al., High efficiency transformation of Tolypocladium geodes conidiospores to phleomycin resistance, Current Genetics, vol. 20, 1991, pp. 309-314.
Drocourt et al., Cassettes of the Streptoalloteichus hindustanus ble gene for transformation of lower and higher eukaryotes to phleomycin resistance, Nucleic Acids Research, vol. 18, No. 13, 1990, p. 4009.
Funakoshi et al., Simple Purification and Properties of Bovine Pancreatic Deoxyribonuclease I, J. Biochem, vol. 88, 1980, pp. 1113-1118.
Huber et al., Structural Basis of the Activation and Action of Trypsin, Accounts of Chemical Research, vol. 11, 1978, pp. 114-122.
Julius et al., Isolation of the Putative Structural Gene for the Lysine-Arginine-Cleaving Endopeptidase Required for Processing of Yeast Prepro-alpha-Factor, Cell, vol. 37, Jul. 1984, pp. 1075-1089.
Keil., B., Chapter 8, Trypsin, The Enzyme, vol. 11, 3rd Edition, 1971, pp. 249-275. Nefsky et al., Preparation of immobilized monomeric actin and its use in the isolation of protease-free and ribonuclease-free pancreatic deoxyribonuclease I, Eur. J. Biochem., vol. 179, 1989. pp. 215-219.
Paudel et al., Purification, Characterization, and the Complete AminAo cid Sequence of Porcine Pancreatic Deoxyribonuclease, J. of Biol. Chem., vol. 216, No. 34, Dec. 5, 1986, pp. 16006-16011.
Sichler et al., The influence of residue 190 in the S1 site of trypsin-like serine proteases on substrate selectivity is universally conserved, FEBS Letters, vol 530. pp. 220-224, 2002.
Thill, et al., Positive and Negative Effects of Multi-copy Integrated Expression Vectors on Protein Expression in Pachia Pastoris, International Symposium on the Genetics of Microorganisms, 1990, pp. 477-490.
Vedvick et al, High-level secretion of biologically active aprotinin from the yeast Pichia pastoris, J. of Industrial Microbiology, vol. 7, 1991, pp. 197-202.
Waters et al, Prepro-alpha-factor Has a Cleavable Signal Sequence, Journal of Biological Chemistry, vol. 263. No. 13, May 5, 1988, pp. 6209-6214.
Werten et al., High-yield Secretion of Recombinant Gelatins by Pichia pastoris, Yeast, vol. 15, 1999, pp, 1087-1096.
Hermodson et al., Determination of the Amino Acid Sequence of Procine Trypsin by Sequenator Analysis, Biochemistry, vol. 12, No. 17, 1973, pp. 3146-3153

* cited by examiner

*Primary Examiner* — Nashaat Nashed
(74) *Attorney, Agent, or Firm* — Scully, Scott, Murphy & Presser, P.C.

(57) ABSTRACT

The present invention relates to the production of a variant of recombinant trypsin with increased substrate specificity for arginine versus lysine in non-animal host organisms. Moreover, the present invention relates to a variant of recombinant trypsin and their production. Also provided are use of recombinant porcine pancreatic trypsin variants for cleavage of precursors of insulins, and kits containing the variant of trypsin.

11 Claims, 5 Drawing Sheets

CLEAVAGE OF PRECURSORS OF INSULINS BY A VARIANT OF TRYPSIN

CROSS REFERENCE TO RELATED APPLICATIONS

This application is a §371 National Filing of International Patent Application No. PCT/EP2006/008380, filed Aug. 26, 2006, which claims priority under 35 U.S.C. §119(a) to European Patent Application No. 05077086.6, filed on Sep. 14, 2005, the disclosures of which are incorporated herein in their entirety.

The present invention relates to the production of a variant of recombinant trypsin with increased substrate specificity for arginine versus lysine in non-animal host organisms. Moreover, the present invention relates to a variant of recombinant trypsin and their production. Also provided are use of recombinant porcine pancreatic trypsin variants for cleavage of precursors of insulins, and kits containing the variant of trypsin.

Trypsin is a serine protease which catalyzes the hydrolytic cleavage of peptides at the carboxyl group of the basic amino acids arginine and lysine (Keil B., (1971). The Enzyme Vol. II, $3^{rd}$ Edition, Editor Boyer, Acad. Press NY. Pp. 249-275). Recombinant porcine pancreatic trypsin has a molecular weight of about 23,000 daltons and an enzymatic activity optimum at pH 8.0.

Trypsin is used in the industrial process of producing insulin and insulin analogs. The production of these biomolecules is described in the literature and several approaches have been chosen. From an economical point of view, the chemical synthesis of human insulin and insulin analogs is not feasible. Therefore, mainly two processes for the production of insulin and insulin analogs currently exist, namely the semi-synthetic approach using porcine insulin as a starting material, and the use of genetically modified microorganisms for the expression of recombinant insulin.

Insulin is a polypeptide of 51 amino acids, which are divided into 2 amino acid chains: the A chain having 21 amino acids and the B chain having 30 amino acids. The chains are connected to one another by means of 2 disulfide bridges. Insulin preparations have been employed for diabetes therapy for many years. Not only naturally occurring insulins are used here, but recently also insulin derivatives and analogs.

Insulin analogs are analogs of naturally occurring insulins, namely human insulin or animal insulins, which differ by substitution of at least one naturally occurring amino acid residue with other amino acid residues and/or addition/removal of at least one amino acid residue from the corresponding, otherwise identical, naturally occurring insulin. The added and/or replaced amino acid residues can also be those which do not occur naturally.

Insulin derivatives are derivatives of naturally occurring insulin or an insulin analog which are obtained by chemical modification. The chemical modification can consist, for example, in the addition of one or more specific chemical groups to one or more amino acids.

Examples for insulin derivatives are B29-N-myristoyl-des(B30) human insulin, B29-N-palmitoyl-des(B30) human insulin, B29-N-myristoyl human insulin, B29-N-palmitoyl human insulin, B28-N-myristoyl $Lys^{B28}Pro^{B29}$ human insulin, B28-N-palmitoyl-$Lys^{B28}Pro^{B29}$ human insulin, B30-N-myristoyl-$Thr^{B29}Lys^{B30}$ human insulin, B30-N-palmitoyl-$Thr^{B29}Lys^{B30}$ human insulin, B29-N—(N-palmitoyl-Y-glutamyl)-des(B30) human insulin, B29-N—(N-lithocholyl-Y-glutamyl)-des(B30) human insulin, B29-N-(ω-carboxyheptadecanoyl)-des(B30) human insulin and B29-N-(ω-carboxyheptadecanoyl) human insulin.

Insulin analogs are described in EP 0 214 826, EP 0 375 437 and EP 0 678 522. EP 0 214 826 relates, inter alia, to substitutions of B27 and B28. EP 0 678 522 describes insulin analogs which have various amino acids, preferably proline, in position B29, but not glutamic acid.

Other insulin analogs are $Lys^{B28}Pro^{B29}$ human insulin, B28 Asp human insulin, human insulin, in which proline in position B28 has been substituted by Asp, Lys, Leu, Val or Ala and where in position B29 Lys can be substituted by Pro; AlaB26 human insulin; des(B28-B30) human insulin; des(B27) human insulin or des(B30) human insulin EP 0 375 437 includes insulin analogs with lysine or arginine in B28, which can optionally additionally be modified in B3 and/or A21.

In EP 0 419 504, insulin analogs are disclosed which are protected against chemical modifications, in which asparagine in B3 and at least one further amino acid in the positions A5, A15, A18 or A21 are modified. In WO 92/00321, insulin analogs are described in which at least one amino acid of the positions B1-B6 is replaced by lysine or arginine.

Important insulin analogs discussed herein further are "insulin glargine" (Gly A(21), Arg B (31), Arg B (32) human insulin) and "insulin glulisine" (Lys B(3), Glu B(29) human insulin).

Recombinant DNA processes allow precursors of insulin or insulin analogs, in particular human proinsulin or proinsulin which has an amino acid sequence and/or amino acid chain length differing from human insulin to be prepared in microorganisms. The proinsulins prepared from genetically modified *Escherichia coli* cells do not have any correctly bonded cystine bridges. A process for obtaining human insulin using *E. coli* (EP 0 055 945) is based on the following process steps:

Fermentation of the microorganism, cell separation, cell disruption, isolation of the insulin or insulin analogue precursor, re-folding to the desired (native) three-dimensional structure by formation of the respective disulfide bonds to yield the pre-pro-insulin(s) ("PPI"), tryptic cleavage of the respective pre-pro-insulin (possibly in presence of Carboxypeptidase B), basic purification, first chromatographic step, eventual enzymatic cleavage to yield human insulin or the respective insulin analogue, second chromatographic step and final purification by HPLC, crystallization and drying.

Tryptic cleavage of the pre-pro-insulins is an enzymatic and complex reaction: the pre-sequence and the C-peptide are cleaved off in this step in order to yield the respective products. For example, in the case of human insulin production, the desired valuables are Arg(B31),Arg(B32)-insulin and Arg(B31)-insulin (DE19821866).

However, tryptic cleavage leads to the formation of many by-products as a result of occurring undesired side-reactions. Trypsin is an endoprotease (serine type) that cleaves peptide bonds at C-terminal arginine (Arg) or lysine (Lys) residues.

Tryptic cleavage of pre-pro-insulin molecules can occur at different cleavage sites simultaneously. Because of the many cleavage sides within a specific pre-pro-insulin molecule, many undesired side-products can be formed during tryptic cleavage reaction. As can be seen in FIG. 1, many of the by-products generated during cleavage reactions are a consequence of peptide bond cleavage on the C-terminal side of Lys instead of Arg residues.

For all pre-pro-insulins, the cleavage site between the pre-sequence and the insulin B chain is monobasic. At this junction, only one cleavage reaction can occur.

At the two other junctions—B-chain/C-peptide and C-peptide/A-chain—different cleavage sites exist. In the case of human insulin and insulin glargine cleavage sites between B-chain/C-peptide and C-peptide/A-chain are both dibasic (Arg-Arg and Lys-Arg, respectively). In addition, cleavage after B29-Lys leads to B30-des-Thr ("des-Thr") formation.

For human insulin only tryptic cleavage after residues B31-Arg and B32-Arg yields valuable products for the B-chain/C-peptide junction, namely B31-Arg insulin ("mono-Arg") and B31-Arg, B32-Arg insulin ("di-Arg"). These products can be summarized as "Arg-insulins". Cleavage after B32-Arg is crucial in the process of producing insulin glargine as only Di-Arg-Insulin can be used. For human insulin and insulin glargine, cleavage after B29-Lys results in des-Thr formation. For insulin glulisine, this cleavage site is monobasic and possible products are Arg-containing species.

Regarding the C-peptide/A-chain, tryptic cleavage after the Arg and not the Lys residue is crucial for yielding valuable products. False cleavage after Lys results in formation of A0-by-products.

In order to overcome the disadvantages of the state of the art it is desired to use in the process of pre-proinsulin cleavage a trypsin enzyme with an enhanced Arg-specificity for the different cleavage sites as exemplary shown in FIG. 1. By increasing the Arg-specificity of a trypsin enzyme—and consequently by decreasing the Lys-specificity—formation of by-products, especially des-Thr and A0-components can be expected. Sichler et al., FEBS Lett. (2002) 530:220-224, examined in human trypsin the impact of an amino acid exchange at position 190 (chymotrypsinogen numbering according to Huber, R. & Bode, W., Acc. Chem. Res. (1978) 11:114-122). It was found that at this position an exchange from wildtype Serine to mutant Alanine caused an increase of the cleavage site selectivity for Arginine and a decrease for Lysine when using artificial substrates. At the same time, the enzymatic activity of the mutant was found to be decreased by a factor of about 2 when compared with the wildtype. Testing of recombinant human wild-type trypsin and human trypsin mutant (amino acid exchange at position 190 from Serine to Alanine) for pre-pro-insulin processing resulted in formation of high amounts of by-products for both enzymes, revealing that an increase in Arg-selectivity could not be assigned for pre-pro-insulin cleavage (see below, Example 1).

In view of the state of the art the problem to be solved is to provide a variant of trypsin which exhibits an increased cleavage site selectivity for Arginine without a major loss of proteolytic activity. Another particular problem to be solved is to provide a variant of trypsin which has an increased cleavage site selectivity for Arginine residues within the cleavage sites for pre-pro-insulin processing as exemplary shown in FIG. 1.

Accordingly, the problem is solved by providing a variant of porcine trypsin with an amino acid exchange at position 172 from Serine to Alanine. In a preferred embodiment the Ser172Ala variant of porcine trypsin is provided by recombinant means. Surprisingly, the enzymatic activity of the Ser172Ala variant of porcine trypsin was found to be almost equal for pre-pro-insulin cleavage reactions when compared to the wildtype enzyme.

The amino acid Serine position 190 examined in human trypsin by Sichler et al. (FEBS Lett. (2002) 530:220-224) corresponds to the Serine at position 172 of porcine trypsin as given in SEQ ID NO: 1. Both positions are part of the so-called S1 site of trypsin-like serine proteases.

One embodiment of the invention therefore is the use of Ser172Ala porcine trypsin in a process of preparing insulin, an insulin analog or an insulin derivative.

Another embodiment of the invention is a process for the preparation of insulin, an insulin analog or an insulin derivative, wherein (a) a pre-pro-insulin, a pre-pro-insulin analog or a pre-pro-insulin derivative is cleaved with Ser172Ala porcine trypsin, (b) the resulting cleavage products are separated and (aa) if one of the resulting cleavage products is an insulin analog or an insulin derivative, this insulin analog or insulin derivative is obtained, or (bb) those cleavage products being precursors of insulin, an insulin analog or an insulin derivative are further processed and the insulin, insulin analog or insulin derivative resulting from such further processing is separated and obtained;

wherein the insulin preferably is human insulin; and the insulin analog is selected from a group comprising $Lys^{B28}Pro^{B29}$ human insulin, B28 Asp human insulin, human insulin, in which proline in position B28 has been substituted by Asp, Lys, Leu, Val or Ala and where in position B29 Lys can be substituted by Pro; AlaB26 human insulin; des(B28-B30) human insulin; des(B27) human insulin and des(B30) human insulin, and the insulin derivative is selected from the group comprising B29-N-myristoyl-des(B30) human insulin, B29-N-palmitoyl-des(B30) human insulin, B29-N-myristoyl human insulin, B29-N-palmitoyl human insulin, B28-N-myristoyl $Lys^{B28}Pro^{B29}$ human insulin, B28-N-palmitoyl-$Lys^{B28}Pro^{B29}$ human insulin, B30-N-myristoyl-$Thr^{B29}Lys^{B39}$ human insulin, B30-N-palmitoyl-$Thr^{B29}Lys^{B39}$ human insulin, B29-N—(N-palmitoyl-Y-glutamyl)-des(B30) human insulin, B29-N—(N-lithocholyl-Y-glutamyl)-des(B30) human insulin, B29-N-(ω-carboxyheptadecanoyl)-des(B30) human insulin and B29-N-(ω-carboxyheptadecanoyl) human insulin.

In a preferred embodiment of the invention the insulin analog is insulin glulisine or insulin glargine.

In a further embodiment of the invention, the mentioned further processing of those cleavage products being precursors of insulin, an insulin analog or an insulin derivative comprises a cleavage of said products with Carboxypeptidase B, except for insulin glargine.

In another embodiment of the invention, the cleavage with Ser172Ala porcine trypsin is performed at an pH-value in the range of 7.5 to 9.5, preferably 8.3; a temperature between 1° C. and 30° C., more preferably between 8 and 15° C., most preferably at 8° C.; and the enzymatic reaction is stopped by acidifying the sample, preferably by adding 1N or 2N HCl solution.

Another embodiment of the invention is Ser172Ala porcine trypsin characterized by the sequence SEQ ID. No.: 3, a DNA encoding Ser172Ala porcine trypsin, preferably characterized by the sequence SEQ ID. No.: 4.

Another embodiment of the invention is a DNA encoding Ser172Ala pre-trypsinogen characterized by the SEQ ID NO:6. The signal peptide of this pre-trypsinogen derives from the alpha factor of *Saccharomyces cerevisiae*.

Another embodiment of the invention is a vector comprising a DNA as described above.

Another embodiment of the invention is a method to produce Ser172Ala porcine trypsin comprising the steps of (a) providing a vector according to claim 16, (b) transforming a microbial host strain with the vector, (c) cultivating the transformed microbial host strain in a growth medium that contains nutrients, whereby the microbial host strain expresses the Ser172Ala porcine trypsin or Ser172Ala porcine trypsinogen, (d) in case the expression product of (c) is Ser172Ala porcine trypsinogen, conversion to mature Ser172Ala procine trypsin, and (e) purifying the Ser172Ala porcine trypsin from the microbial host strain and/or the growth medium, in particular wherein the microbial host strain is a methylotrophic yeast strain selected from a group comprising *Hansenula*, *Pichia*, *Candida* and *Torulopsis* species; preferably wherein the microbial host strain is selected from a group comprising *Pichia pastoris*, *Hansenula polymorpha*, *Candida boidinii* and *Torulopsis glabrata*.

In this document, the terms "porcine trypsin variant" and "variant of porcine trypsin" denote a protein that is a variant, i.e. an allelic form of the mature porcine pancreatic trypsin protein isoform 1, generated by way of amino acid substitution at position 172 according to SEQ ID NO: 1.

For purposes of shorthand designation of the porcine trypsin variant described herein, it is noted that the number refers to the amino acid residue/position along the amino acid sequence of the mature porcine pancreatic trypsin as given in SEQ ID NO: 1. Amino acid identification uses the three-letter abbreviations as well as the single-letter alphabet of amino acids, i.e., Asp D Aspartic acid, Ile I Isoleucine, Thr T Threonine, Leu L Leucine, Ser S Serine, Tyr Y Tyrosine, Glu E Glutamic acid, Phe F Phenylalanine, Pro P Proline, H is H Histidine, Gly G Glycine, Lys K Lysine, Ala A Alanine, Arg R Arginine, Cys C Cysteine, Trp W Tryptophan, Val V Valine, Gln Q Glutamine, Met M Methionine, Asn N Asparagine. An amino acid at a particular position in an amino acid sequence is given by its three-letter abbreviation and a number. Accordingly, Ser172 denotes the Serine residue at amino acid position 172 in SEQ ID NO: 1. A substitution by a different amino acid is given as the three-letter abbreviation added after the number indicating the position. E.g., "Ser172Ala" denotes the substitution of Ser at position 172 in SEQ ID NO: 3 by Ala.

The term "increased cleavage site selectivity" of a variant of trypsin denotes a shift of specificity for hydrolytic cleavage, whereby for the variant the shift leads to a preferred cleavage at the carboxyl group of arginine rather than lysine.

When tryptic activity is quantified, the present document refers to "units" (U). The proteolytic activity of trypsin and variants thereof is quantified using a photometric assay using as substrates Chromozym TRY, Chromozym TH and Chromozym PL (Roche Diagnostics GmbH). The "specific proteolytic activity" or "specific activity" of a given preparation is defined as the number of units per mg of protein in the preparation, determined by the method described in Example 9.

A "methylotrophic yeast" is defined as a yeast that is capable of utilising methanol as its carbon source. The term also comprises laboratory strains thereof. In case a methylotrophic yeast strain is auxotrophic and because of this needs to be supplemented with an auxiliary carbon-containing substance such as, e.g. histidine in the case of a methylotrophic yeast strain unable to synthesise this amino acid in sufficient amounts, this auxiliary substance is regarded as a nutrient but not as a carbon source.

A "vector" is defined as a DNA which can comprise, i.e. carry, and maintain the DNA fragment of the invention, including, for example, phages and plasmids. These terms are understood by those of skill in the art of genetic engineering. The term "expression cassette" denotes a nucleotide sequence encoding a pre-protein, operably linked to a promoter and a terminator. As for vectors containing an expression cassette, the terms "vector" and "expression vector" are used as synonyms.

The term "oligonucleotide" is used for a nucleic acid molecule, DNA (or RNA), with less than 100 nucleotides in length.

"Transformation" means introducing DNA into an organism, i.e. a host organism, so that the DNA is replicable, either as an extrachromosomal element or by chromosomal integration.

The term "expression" and the verb "to express" denote transcription of DNA sequences and/or the translation of the transcribed mRNA in a host organism resulting in a pre-protein, i.e. not including post-translational processes.

A nucleotide sequence "encodes" a peptide or protein when at least a portion of the nucleic acid, or its complement, can be directly translated to provide the amino acid sequence of the peptide or protein, or when the isolated nucleic acid can be used, alone or as part of an expression vector, to express the peptide or protein in vitro, in a prokaryotic host cell, or in a eukaryotic host cell.

A "promoter" is a regulatory nucleotide sequence that stimulates transcription. These terms are understood by those of skill in the art of genetic engineering. Like a promoter, a "promoter element" stimulates transcription but constitutes a sub-fragment of a larger promoter sequence.

The term "operably linked" refers to the association of two or more nucleic acid fragments on a single vector so that the function of one is affected by the other. For example, a promoter is operably linked with a coding sequence, i.e. a nucleotide sequence encoding a protein or a pre-protein, when it is capable of affecting the expression of that coding sequence, i.e., that the coding sequence is under the transcriptional control of the promoter.

The term "polypeptide" or "protein" denotes a polymer composed of more than 90 amino acid monomers joined by peptide bonds. The term "peptide" denotes an oligomer composed of 90 or fewer amino acid monomers joined by peptide bonds. A "peptide bond" is a covalent bond between two amino acids in which the α-amino group of one amino acid is bonded to the α-carboxyl group of the other amino acid.

The term "pro-protein", "pro-protein form", "Zymogen", "trypsinogen", "pre-protein" or "pre-pro-protein" denotes a primary translation product that is a precursor of a mature protein, i.e. in this case a protein results from post-translational processing of a pre-protein.

The term "post-translational processing" denotes the modification steps a pre-protein or a pre-pro protein is subjected to, in order result in a mature protein in a cellular or extracellular compartment.

A "signal peptide" is a cleavable signal sequence of amino acids present in the pre-protein or a pre-pro-protein form of a secretable protein. Proteins transported across the cell membrane, i.e. "secreted", typically have an N-terminal sequence rich in hydrophobic amino acids, typically about 15 to 30 amino acids long. Sometime during the process of passing through the membrane, the signal sequence is cleaved by a signal peptidase (Alberts, B., Johnson, A., Lewis, J., Raff, M., Roberts, K., Walter, P. (eds), Molecular Biology of the Cell, fourth edition, 2002, Garland Science Publishing). Many sources of signal peptides are well known to those skilled in the art and can include, for example, the amino acid sequence of the α-factor signal peptide from Saccharomyces cerevisiae and the like. Another example is the porcine signal peptide of the native porcine pancreatic trypsinogen pre protein according to SEQ ID NO: 5, position 1-16. In general, the pre-protein N-terminus of essentially any secreted protein is a potential source of a signal peptide suitable for use in the present invention. A signal peptide can also be bipartite comprising two signal peptides directing the pre-protein to a first and a second cellular compartment. Bipartite signal peptides are cleaved off stepwise during the course of the secretory pathway. A specific example therefor is the prepro peptide of the α-factor from Saccharomyces cerevisiae (Waters et al., J. Biol. Chem. 263 (1988) 6209-14).

Pre-proteins with an N-terminal signal peptide are directed to enter the "secretory pathway". The secretory pathway comprises the processes of post-translational processing and finally results in secretion of a protein. Glycosylation and the formation of disulfide bonds are processes that are part of the secretory pathway prior to secretion. In the present document it is understood that proteins secreted by methylotrophic yeast strains have passed through the secretory pathway.

DETAILED DESCRIPTION OF THE INVENTION

All trypsin-like serine proteases share a substrate preference for a basic residue, Lysine or Arginine. While amino acid exchange mutation at a serine corresponding to position 190 of human pancreatic trypsin leads to the desired shift in specificity regarding artificial substrates, a decrease of proteolytic activity is the consequence.

In addition, evaluation of the human trypsin mutant revealed that the observed shift in specificity towards Arginine residues using artificial substrates could not be assigned to pre-pro insulin processing. Example 1 illustrates conversion of a pre-pro-insulin with the human Serine-190Alanine trypsin mutant. High amounts of by-products, mainly B30-des-Thr- and A0-components, are formed during reaction.

It has not been shown to which extent this effect equally applies to all trypsin-like serine proteases. One way to elucidate this question is to introduce the Ser-Ala exchange mutation into the amino acid sequences of other mammalian trypsin species at a site within each respective polypeptide sequence corresponding to position 190 of human pancreatic trypsin isotype I. Doing so the inventors surprisingly found that such an exchange mutation in porcine pancreatic trypsin increases the cleavage site selectivity for Arginine in pre-pro insulin processing and at the same time maintains a higher level of proteolytic activity.

A person skilled in the art is well aware of methods to substitute one or more amino acid residues in a protein. Example 2 illustrates how an amino acid exchange mutant can be engineered on the level of the coding DNA sequence. However, other methods are possible. In the present invention, the synthetic nucleotide sequence encoding the Ser172Ala mutant of porcine pancreatic trypsin as given in Seq ID NO: 4 was expressed in microbial host organisms.

The trypsin variant is preferably produced as heterologous proteins in microbial host organisms such as bacteria and fungi. The person skilled in the art is well aware of bacterial expression systems that exist for a variety of prokaryotic hosts such as E. coli, Bacillus and Staphylococcus species, to name but a few. Even more preferred microbial host organisms are fungi. An example for a preferred fungal genus is Aspergillus. Yet, even more preferred are yeast species such as species of the genera Saccharomyces or Schizosaccharomyces. Yet, even more preferred are strains of methylotrophic yeast species.

Methylotrophic yeasts have the biochemical pathways necessary for methanol utilization and are classified into four genera, based upon cell morphology and growth characteristics: Hansenula, Pichia, Candida, and Torulopsis. The most highly developed methylotrophic host systems utilize Pichia pastoris (Komagataella pastoris) and Hansenula polymorpha (Pichia angusta).

Expression of heterologous proteins in yeast is described in U.S. Pat. No. 5,618,676, U.S. Pat. No. 5,854,018, U.S. Pat. No. 5,856,123, and U.S. Pat. No. 5,919,651.

Yeast organisms produce a number of proteins that are synthesized intracellularly but have a function outside the cell. These extracellular proteins are referred to as secreted proteins. Initially the secreted proteins are expressed inside the cell in the form of a precursor, a pre-protein or a pre-pro-protein containing an N-terminal signal peptide ensuring effective direction of the expressed product into the secretory pathway of the cell, across the membrane of the endoplasmic reticulum. The signal peptide is generally cleaved off from the desired product during translocation. Cleavage is effected proteolytically by a signal peptidase. A particular sub-sequence of amino acids of the signal peptide is recognised and cleaved by the signal peptidase. This sub-sequence is referred to as signal peptidase cleavage site. Once having entered the secretory pathway, the protein is transported to the Golgi apparatus. From the Golgi apparatus the proteins are distributed to the plasma membrane, lysosomes and secretory vesicles.

Secreted proteins are confronted with different environmental conditions as opposed to intracellular proteins. Part of the processes of the secretory pathway is to stabilise the maturing extracellular proteins. Therefore, pre-proteins that are passed through the secretory pathway of yeast undergo specific posttranslational processing. For example, processing can comprise the generation of disulfide bonds to form intramolecular cross-links. Moreover, certain amino acids of the protein can be glycosylated.

Several approaches have been suggested for the expression and secretion in yeast of proteins heterologous to yeast. EP 0 116 201 describes a process by which proteins heterologous to yeast are transformed by an expression vector harboring DNA encoding the desired protein, a signal peptide and a peptide acting as a signal peptidase cleavage site. A culture of the transformed organism is prepared and grown, and the protein is recovered from culture media. For use in yeast cells a suitable signal peptide has been found to be the α-factor signal peptide from Saccharomyces cerevisiae (U.S. Pat. No. 4,870,008).

During secretion, the yeast enzyme KEX-2 is the signal peptidase which recognizes a Lysine-Arginine sequence as its cleavage site in the pre-protein. KEX-2 cleaves at the junction to the sequence of the desired protein. As a result, the desired gene product is released and free of the leader portions, i.e. the signal peptide of the pre-protein. KEX-2 endoprotease was originally characterised in *Saccharomyces* yeast where it specifically processes the precursor of mating type α-factor and a killer factor (Julius, D., et al., Cell 37 (1984) 1075-1089). Methylotrophic yeast species such as *Pichia pastoris* share the KEX-2-type protease (similar role and function) with *Saccharomyces cerevisiae* (Werten, M. W., et al., Yeast 15 (1999) 1087-1096).

A well-established methylotrophic yeast species exemplarily described as host for high-level recombinant protein expression is *Pichia pastoris* (U.S. Pat. No. 4,683,293, U.S. Pat. No. 4,808,537, U.S. Pat. No. 4,812,405, U.S. Pat. No. 4,818,700, U.S. Pat. No. 4,837,148, U.S. Pat. No. 4,855,231, U.S. Pat. No. 4,857,467, U.S. Pat. No. 4,879,231, U.S. Pat. No. 4,882,279, U.S. Pat. No. 4,885,242, U.S. Pat. No. 4,895,800, U.S. Pat. No. 4,929,555, U.S. Pat. No. 5,002,876, U.S. Pat. No. 5,004,688, U.S. Pat. No. 5,032,516, U.S. Pat. No. 5,122,465, U.S. Pat. No. 5,135,868, U.S. Pat. No. 5,166,329, WO 00/56903). In the absence of glucose, *Pichia pastoris* uses methanol as a carbon source which at the same time is a hallmark of a methylotrophic organism. The alcohol oxidase (AOX1) promoter given in SEQ ID NO: 7 controls expression of alcohol oxidase, which catalyses the first step in methanol metabolism. Typically, 30% of the total soluble protein in methanol-induced cells is alcohol oxidase. Several *Pichia* expression vectors carry the AOX1 promoter and use methanol to induce high-level expression of desired heterologous proteins. Expression constructs also integrate into the *Pichia pastoris* genome, creating a transformed and genetically stable host.

Using an expression vector encoding a heterologous pre-protein comprising a signal peptide or a signal peptide with a signal peptidase cleavage site, and a desired protein, methylotrophic yeast strains such as *Pichia pastoris* strains can be manipulated in order to secrete the desired product into the growth medium from which the secreted protein can be purified.

It may be advantageous to produce nucleotide sequences encoding the pre-protein possessing a substantially different codon usage. Codons may be selected to increase the rate at which expression of the pre-protein occurs in a particular yeast expression host in accordance with the frequency with which particular codons are utilised by the host. Other reasons for substantially altering the nucleotide sequence encoding the pre-protein, without altering the encoded amino acid sequences, include the production of RNA transcripts having more desirable properties, such as a greater half-life, than transcripts produced from the naturally occurring sequence.

Example 3 illustrates the cloning steps to provide an expression vector encoding the trypsin variant. Using a vector comprising the nucleotide sequence encoding the pre-protein that is competent for expression, e.g. operably linked to a promoter or promoter element and to a terminator or terminator element, as well as to sequences required for efficient translation, the host organism is transformed with the vector, and transformants are selected.

On the one hand, expression yield is dependent on proper targeting of the desired product, e.g. to the secretory pathway by means of a signal peptide such as the α-factor signal peptide from *Saccharomyces cerevisiae* or the porcine signal peptide of the native porcine pancreatic trypsinogen. Example 4 provides a transformed microbial host and Example 5 shows how expression of the trypsin variant can be achieved. Accordingly, the primary translational product comprises a signal peptide which directs the polypeptide into the secretory pathway. Examples 6 illustrates the measurement of tryptic activity in the supernatant of transformed methylotrophic yeast.

On the other hand, expression yield can be increased by increasing the dosage of the gene encoding the desired product. Thus, the copy number of the expression construct, that is the expression vector or the expression cassette, in the host organism is amplified. One way to accomplish this is by multiple transformation of an expression vector encoding the desired product. Another way is to introduce the gene encoding the desired product into the host organism using a first and a second expression vector, whereby the second expression vector is based on a selectable marker which differs from the selectable marker used in the first expression vector. The second expression vector encoding the same desired product can even be introduced when the host organism already carries multiple copies of a first expression vector (U.S. Pat. No. 5,324,639; Thill, G. P., et al., Positive and Negative Effects of Multi-Copy Integrated Expression in *Pichia pastoris*, International Symposium on the Genentics of Microorganisms 2 (1990), pp. 477-490; Vedvick, T., et al., J. Ind. Microbiol. 7 (1991) 197-201; Werten, M. W., et al., Yeast 15 (1999) 1087-1096). Example 7 describes how the yield of expression of the trypsin variant can be increased in order to provide a yeast clone for production at an industrial scale.

Transformants are repeatedly analysed with respect to the yield of recombinant protein secreted into the growth medium. Transformants secreting the highest quantities of enzymatically active recombinant protein are selected.

Secretion of the porcine trypsin variant into the growth medium directs the mature recombinant protein to the extra-cytoplasmic space from where it diffuses into the growth medium. Transformed methylotrophic yeast grown in liquid culture secretes the recombinant porcine pancreatic trypsin variant into the liquid growth medium, i.e. the liquid culture medium. This allows a very efficient separation of yeast biomass from the recombinant protein using, e.g. filtration techniques. As a result, the recombinant porcine trypsin variant purified from this source is very efficiently separated from other enzyme activities such as ribonuclease or other (non-tryptic) protease activities.

Therefore, a first preferred embodiment of the invention is a variant, by way of amino acid substitution, of porcine pancreatic trypsin isotype I, wherein the amino acid Serin in position 172 substitutes for the amino acid residue Alanin, numbered from the N-terminus of porcine pancreatic trypsin isotype I according to SEQ ID NO: 1, to form a porcine pancreatic trypsin variant with trypsin activity.

Preferably, the variant of porcine pancreatic trypsin has an increased cleavage site selectivity towards hydrolytic cleavage at the carboxyl group of the amino acid arginine, rather than hydrolytic cleavage at the carboxyl group of the amino acid lysine.

More preferred, the isolated variant exhibits the increased selectivity when an insulin precursor polypeptide or an analogue thereof is used as a substrate.

In yet another preferred embodiment of the invention, the specific proteolytic activity of the porcine trypsin variant is 100% compared to wildtype porcine pancreatic trypsin. Thus, when produced and purified under equivalent conditions, the specific trypsin activity of the variant of recombinant porcine pancreatic trypsin is 100% when compared to the unchanged porcine pancreatic trypsin, that is the wild-type form.

Another preferred embodiment of the invention is a method to produce a variant of porcine pancreatic trypsin comprising the steps of (a) providing a vector comprising a nucleotide sequence that encodes the variant of porcine pancreatic trypsin, (b) transforming a microbial host strain with the vector, (c) cultivating the transformed microbial host strain in a growth medium that contains nutrients, whereby the microbial host strain expresses the variant of recombinant porcine pancreatic trypsin, and (d) purifying the variant of recombinant porcine pancreatic trypsin from the microbial host strain and/or the growth medium.

Translation efficiency of a heterologous protein can be improved by adapting the codons of the nucleotide sequence encoding the heterologous protein according to the preferred codons in the host organism. Thus, in a preferred embodiment of the invention, the nucleotide sequence that encodes the variant of recombinant porcine pancreatic trypsin is SEQ ID NO: 4.

In an even more preferred embodiment of the invention, (a) the vector comprises a nucleotide sequence that encodes a pre-protein consisting of the recombinant porcine pancreatic trypsinogen and a signal peptide as given in SEQ ID NO: 6, (b) the microbial host strain is a methylotrophic yeast strain, (c) the growth medium contains methanol as a carbon source, (d) the methylotrophic yeast strain expresses and secretes the variant of recombinant porcine pancreatic trypsin, and (e) the variant of porcine pancreatic trypsin is purified from the growth medium.

Yeast-derived as well as non-yeast-derived eukaryotic signal peptides other than those particularly mentioned can be used for the same purpose. Although the signal peptides might not be cleavable by the signal peptidase, a signal peptidase cleavage peptide can be inserted into the pre-protein amino acid sequence, that is between the amino acid sequence of the signal peptide and the amino acid sequence of the variant recombinant porcine pancreatic trypsin polypeptide. Therefore, in yet another very much preferred embodiment of the invention, the signal peptide contains a signal peptidase cleavage site which is located adjacent to the first (N-terminal) amino acid of the recombinant porcine pancreatic trypsinogen.

In another preferred embodiment of the invention, the nucleotide sequence encoding the pre-protein is operably linked to a promoter or promoter element. It is preferred that the vector is a plasmid capable of being replicated as an episome in the methylotrophic yeast strain. It is furthermore preferred that an artificial chromosome capable of being replicated in the methylotrophic yeast strain contains the vector. Yet, it is most preferred that a chromosome of the methylotrophic yeast strain contains the vector as an integrate.

Thus, in the preferred method using methylotrophic yeast strains and particularly in *Pichia pastoris* strains, the vector encodes an amino acid sequence for a variant of porcine pancreatic trypsinogen pre-protein that enters the secretory pathway.

In a further preferred embodiment of the invention, the methylotrophic yeast strain is a *Hansenula, Pichia, Candida* or *Torulopsis* species. It is very preferred that the methylotrophic yeast strain is selected from the group consisting of *Pichia pastoris, Hansenula polymorpha, Candida boidinii* and *Torulopsis glabrata*. It is even more preferred that the methylotrophic yeast strain is the *Pichia pastoris* strain with the American Type Culture Collection accesssion number 76273 or a derivative thereof.

Another preferred embodiment of the invention is a *Pichia pastoris* strain with a chromosome that contains a vector comprising a nucleotide sequence that encodes a pre-protein consisting of the variant of recombinant porcine pancreatic trypsin and a signal peptide, operably linked with the *Pichia pastoris* AOX1 promoter according to SEQ ID NO: 7 or a promoter element thereof.

The person skilled in the art is aware of the fact that the yield of secreted heterologous protein, such as a variant of porcine pancreatic trypsin, obtainable from growth medium, such as liquid growth medium, can be increased when the number of copies of the nucleotide sequence encoding the pre-protein from which the heterologous protein is expressed and secreted, is increased. Thus, the yield of secreted heterologous protein obtainable from growth medium can be increased when number of copies of the vector in the genome of the methylotrophic yeast strain is increased. For example, the copy number of the vector can be increased by subjecting the methylotrophic yeast strain to repeated transformations of the vector and repeated selection rounds using increasing concentrations of the selective agent against which the selective marker comprised in the vector confers resistance (U.S. Pat. No. 5,324,639; Thill, G. P., et al., Positive and Negative Effects of Multi-Copy Integrated Expression in *Pichia pastoris*, International Symposium on the Genentics of Microorganisms 2 (1990), pp. 477-490; Vedvick, T., et al., J. Ind. Microbiol. 7 (1991) 197-201).

An example for a selective marker is the Sh ble gene, that is the Zeocin™ resistance gene (Drocourt, D., et al., Nucleic Acids Res. 18 (1990) 4009; Carmels, T., et al., Curr. Genet. 20 (1991) 309-314). The protein encoded by the Sh ble gene binds Zeocin™ stoichiometrically and with a strong affinity. The binding of Zeocin™ inhibits its toxic activity thereby selecting for transformants containing the Sh ble gene. It is known to a person skilled in the art that increasing the concentration of Zeocin™ as the selective agent in the medium selects for an increase in the number of copies of the vector expressing the Sh ble gene. It is therefore advantageous to use a vector with the Sh ble gene as a selectable marker to generate by repeated transformation multiple transformants of the methylotrophic yeast strain containing multiple copies of the vector. It is furthermore advantageous that transformations are repeated and selection for even more resistant transformants is repeated until for the transformed methylotrophic yeast strain no further increase of the level of resistance to Zeocin™ is obtained anymore or no further increase of the Zeocin™ concentration in the selection medium is possible anymore.

A person skilled in the art is familiar with the purification of recombinantly expressed and secreted porcine pancreatic trypsin by means of chromatography (Funakoshi, A., et al., J. Biochem. (Tokyo) 88 (1980) 1113-1138; Paudel, H. K., and Liao, T. H., J. Biol Chem. 261 (1986) 16006-16011; Nefsky, B., and Bretscher, A., Eur. J. Biochem. 179 (1989) 215-219). It is preferred that a variant of porcine pancreatic trypsinogen in the growth medium is purified using ion exchange chromatography. Downstream processing steps leading to the purified product are described in Example 8. Production of wildtype porcine pancreatic trypsin isoform I was done similarly except that the wildtype coding sequence was used to construct the expression vector.

Yet, another preferred embodiment of the invention is a variant of porcine pancreatic trypsin isotype I, by one of the methods described above. Another embodiment of the invention is the use of the variant of porcine pancreatic trypsin. for pre-pro-insulin processing. The benefits of the use of the Ser172Ala variant of porcine trypsin for enzymatic cleavage of different pre-pro-insulins are described in Examples 10-12. The following examples, references, sequence listing and figures are provided to aid the understanding of the present invention, the true scope of which is set forth in the appended claims. It is understood that modifications can be made in the procedures set forth without departing from the spirit of the invention.

Figure 1:
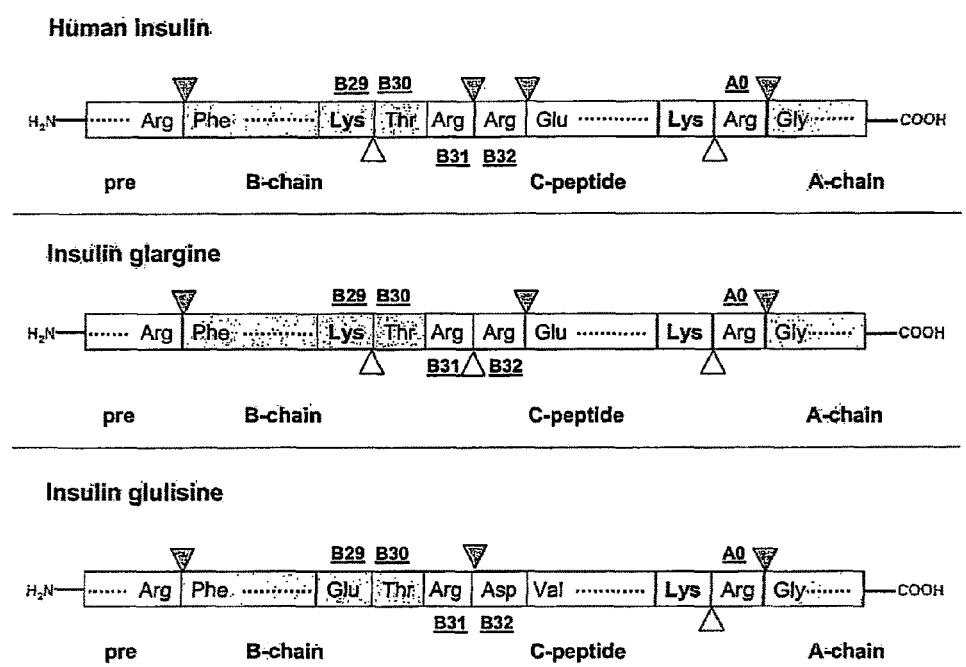
FIG. 1: Scheme of main tryptic cleavage sites for the pre-pro-insulins of human insulin, Insulin glargine and Insulin glulisine. Filled triangles denote cleavage sites yielding product(s), open triangles denote cleavage sites yielding by-products. The disulfide bonds of the pre-pre insulins are not displayed.
Figure 2:
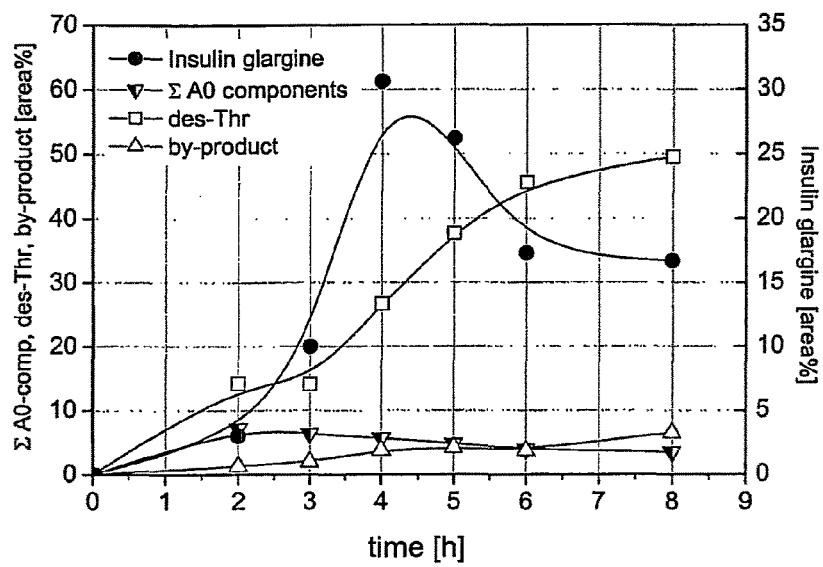
FIG. 2: Pre-pro-insulin glargine cleavage with recombinant, wild-type human trypsin (Example 1)
Figure 3:
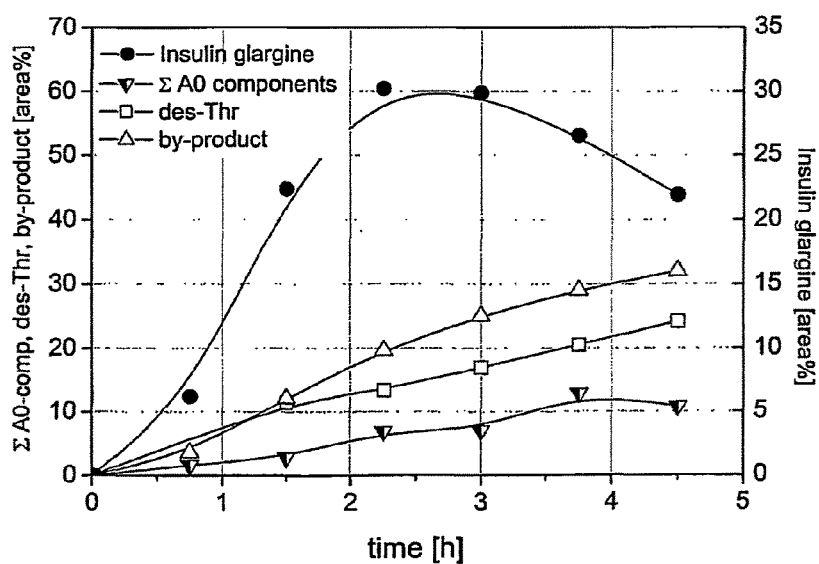
FIG. 3: Pre-pro-insulin glargine cleavage with recombinant, Serine190Alanine human trypsin variant (Example 1)
Figure 4:
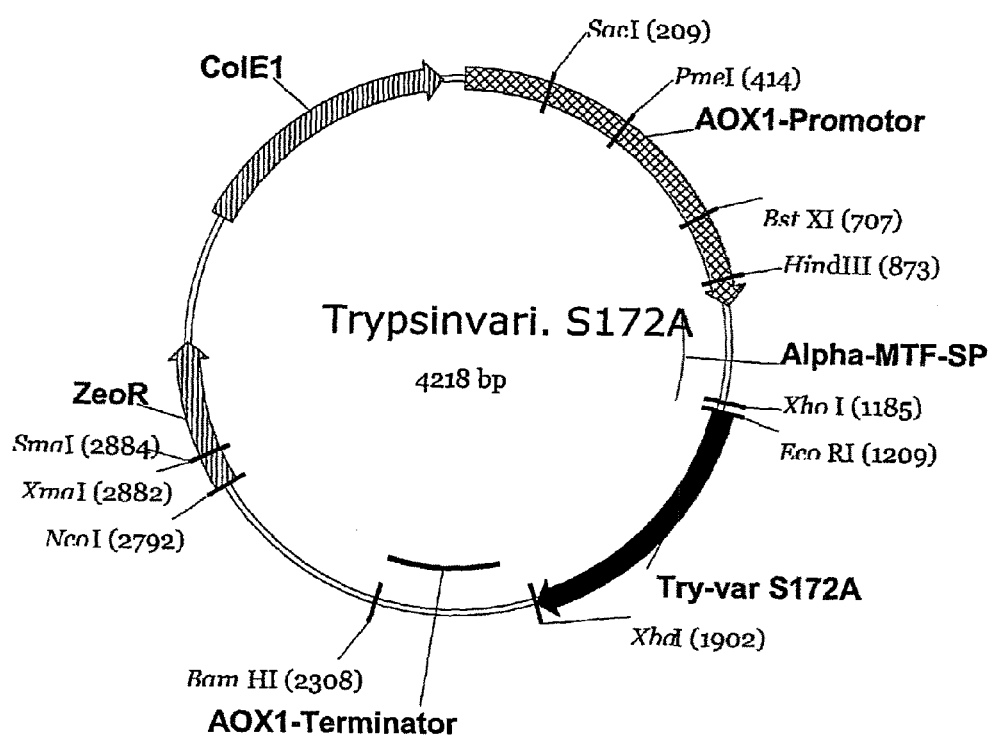
FIG. 4: Map of the plasmid pTry-Ser172Ala which is a derivative of the commercially available plasmid pPICZαA (Invitrogen) that confers resistance to Zeocin™. The insert denoted TrySer172Ala is the synthetic DNA sequence encoding the variant of recombinant porcine secreted trypsinogen that carries the Ser172Ala amino acid substitution, and that is fused to the nucleotide sequence encoding the α-factor signal peptide from *Saccharomyces cerevisiae*. "AOX1-Prom" denotes the *Pichia pastoris* AOX1 promoter, "Term" denotes the *Pichia pastoris* AOX1 terminator.

Generally, in the following examples the methods suggested and described in the Invitrogen manuals "*Pichia* Expression Kit" Version M 011102 25-0043, "pPICZ A, B, and C" Version D 110801 25-0148, "pPICZα A, B, and C" Version E 010302 25-0150, and "pPIC9K" Version E 030402 25-0106 were applied. Reference is also made to further vectors, yeast strains and media mentioned therein. Basic methods of molecular biology were applied as described in Sambrook, Fritsch & Maniatis, Molecular Cloning, A Laboratory Manual, 3rd edition, CSHL Press, 2001.

HPLC Method:

Stationary phase: Nucleosil 120-5 C18, Macherey & Nagel, 250×4 mm; Mobile phase A: 45 mM sodium phosphate buffer (pH 2.5), 315 mM NaCl, 25% (v/v) acetonitrile; Mobile Phase B: 45 mM sodium phosphate buffer (pH 2.5), 55 mM NaCl, 65% (v/v) acetonitrile; Gradient: linear, from 6% phase B to 10% phase B within 30 min.

The following examples are intended to illustrate the present invention without limiting it.

Example 1

Cleavage of Pre-Pro-Insulin Glargine Using Recombinant Human Wild-Type Trypsin and Serine 190Alanine Human Trypsin Variant These experiments were conducted at 8° C. and a pH value of 8.3 (buffered solution) and were performed up to the 50 mL scale.

The PPI solution was filled in an appropriate thermostated reaction vessel and the reaction was started by addition of the enzyme preparation. Samples were taken after definite time intervals; the enzymatic reaction was immediately stopped by acidifying the sample solution by a 1 N or 2 N HCl solution. The concentration of the respective products were determined by HPLC.

Example 2

Mutagenesis of the Synthetic Nucleotide Sequence that Encodes Porcine Pancreatic Trypsinogen Generally, standard methods of molecular biology were applied as described in Sambrook, Fritsch & Maniatis, Molecular Cloning, A Laboratory Manual, 3rd edition, CSHL Press, 2001. The method explained below is a specific application of a very general method that is also known as "site-directed mutagenesis".

Mutations were generated in a site-directed fashion using the polymerase chain reaction (PCR). In order to mutate a desired codon, i.e. a base triplett, a pair of complementary single-stranded DNA oligonucleotides representing a variant portion of the synthetic nucleotide sequence encoding porcine pancreatic trypsinogen were designed and synthesised. The single-stranded DNA oligonucleotides were identical or complementary to the sequence given in SEQ ID NO: 2 except for the triplett sequence to be mutated. Typically, a DNA oligonucleotides had a length of about 20 to 45 nucleotides; the triplett sequence to be mutated or its complement was located in the central portion of the DNA oligonucleotide comprising it, and was flanked on both sides by about 10 to 12 nucleotides. The DNA oligonucleotides were designed such that hybridisation of the DNA oligonucleotides to the 'wild-type' recombinant porcine pancreatic trypsinogen DNA (according to SEQ ID NO: 2) resulted in hybrids with a central mismatch but with intact base pairing at the flanks of the mismatch, including the 5' and 3' ends of each DNA oligonucleotide.

Additionally, two single-stranded DNA oligonucleotide primers were provided, of which the first one, designated "5' trypsin" (SEQ IN NO: 8) comprised the 5'-terminal 9 nucleotides of SEQ ID NO: 2 and the second, designated "3' trypsin" (SEQ IN NO: 9) comprised the sequence complementary to the 3'-terminal 12 nucleotides of SEQ ID NO: 2. The two primers were designed to comprise restriction endonuclease cleavage sites. Therefore, the first and the second primer were extended and included adjacent sequences that were flanking the synthetic nucleotide sequence of SEQ ID NO: 2. "5' trypsin" contained an EcoRI and a 3' Xba I site.

A nucleotide sequence that encoded a variant, by way of substitution of an amino acid, of the wild-type mature porcine pancreatic trypsin protein was synthesised by means of several PCR-based steps.

A first and a second PCR was carried out using as a template double-stranded DNA comprising the nucleotide sequence according to SEQ ID NO: 2 that was present as an insert in a vector. The vector sequences flanking the insert were such that during PCR the primers "5' trypsin" and "3' trypsin" matched perfectly when annealed. The first PCR was made using a pair of primers consisting of the "5' trypsin" primer and a first single-stranded DNA oligonucleotide comprising the mutated, i.e. variant triplett sequence, whereby the two primers annealed to opposite template DNA strands. The second PCR was made accordingly, using the "3' trypsin" primer and a second single-stranded DNA oligonucleotide, that was complementary to the first one. As a result, the first and the second PCR generated two intermediate products: A 5' and a 3' portion of a nucleotide sequence encoding a variant of recombinant porcine pancreatic trypsin, whereby the 5' portion carried the mutated sequence at its 3' end and, vice versa, the 3' portion carried the mutated sequence at its 5' end.

The resulting two intermediate amplification products were analysed by agarose gel electrophoresis, the desired fragments were excised and DNA was isolated from agarose blocks using the "QIAquick Gel Extraction Kit" (Qiagen, catalogue no. 28704).

A third PCR was carried out subsequently, in order to fuse the two portions. To this end, the two portions were united in a single PCR and five PCR cycles were run without any additional upstream and downstream primers added. During these cycles a few full-length products were formed, whereby the annealing temperature that was used was calculated for the overlapping sequence of the 5' portion and 3' portion. Subsequently, the primers "5' trypsin" and "3' trypsin" were added and 25 more PCR cycles were run, whereby the annealing temperature used here corresponded to the added primer with the lower melting temperature.

A mutated full-length DNA fragment was subsequently inserted into a cloning vector using the "PCR cloning kit— blunt end" (Roche Diagnostics GmbH, Mannheim; catalogue no. 1 939 645). The DNA fragment was verified by means of restriction enzyme analysis and sequencing. The verified DNA fragment was then excised by means of cleavage with Xho I and Not I and inserted into Pichia pastoris expression vectors that were cleaved with the same restriction enzymes (see Example 3 and Example 5).

Ser172Ala: The base triplett "TCT" found in SEQ ID NO: 2 at position 528-531 was substituted by "GCT". To this end, in a first PCR the DNA oligonucleotide "5'-Try-Ser172Ala" (SEQ ID NO: 10) was used as a primer in combination with "3'-trypsin", and in a second PCR "3'-Try-Ser172Ala" (SEQ ID NO: 11) was used as a primer in combination with "5'-trypsin". The isolated intermediate fragments were subsequently used for the third PCR, in order to generate the full-length product.

Example 3

Cloning of the Artificial DNA Encoding a Variant Recombinant Porcine Pancreatic Trypsinogen in pPICZαA-Derived Expression Vectors The DNA fragment encoding the variant recombinant porcine pancreatic trypsinogen that was generated from PCR fragments (see Example 2) was excised with EcoRI and XbaII (Roche Diagnostics GmbH). The fragment was isolated using the "QIAquick Gel Extraction Kit" according to the instructions of the manufacturer.

The fragment was ligated into the pPICZαA vector, thereby fusing the nucleotide sequence encoding the variant recombinant porcine pancreatic trypsinogen to the nucleotide sequence encoding the α-factor signal peptide from Saccharomyces cerevisiae. Before the ligation reaction, the vector was similarly cleaved with EcoRI and XbaI, and isolated.

The cloning procedure followed inserted the nucleotide sequence encoding the variant recombinant porcine pancreatic trypsinogen directly and in frame after the nucleotide sequence encoding the α-factor signal peptide from Saccharomyces cerevisiae.

The nucleotide sequence encoding the recombinant pre-proprotein as given in SEQ ID NO: 6 were under the control of the P. pastoris AOX-1 promoter (SEQ IN NO.: 7) which, e.g. in Pichia pastoris, is inducible by methanol.

Construction was accomplished by joining in a total volume of 10 µl 20 ng of linearised vector fragment (in a volume of 1 µl), 100 ng of cleaved PCR fragment (in 3 µl), and incubation overnight at 16° C. in the presence of T4 DNA ligase (Roche Diagnostics GmbH) according to the instructions of the manufacturer. 5 µl of the ligation preparation were subsequently used to transform competent E. coli XL1 Blue cells (Stratagene), in a total volume of 205 µl. Following incubation on ice for 30 min, cells were heat-shocked at 42° C. for 90 sec. Subsequently, cells were transferred into 1 ml LB medium and incubated for 1 h at 37° C. to allow for expression of selection markers. Aliquots were plated afterwards on LB plates containing 100 µg/ml Zeocin and incubated for 15 h at 37° C. Resistant clones were picked, plasmids were isolated (Sambrook, Fritsch & Maniatis, Molecular Cloning, A Laboratory Manual, 3rd edition, CSHL Press, 2001) and tested by means of restriction analysis as well as sequence analysis. Construct clones verified to be free of errors and cloning artifacts were selected. The expression vector harbouring a variant recombinant porcine pancreatic trypsin with the α-factor signal peptide from Saccharomyces cerevisiae were designated pTry-Ser172Ala, Example 4

Transformation of Pichia pastoris with pPICZαA-Derived pTry-Ser172Ala Expression Vectors The host strains used were Pichia pastoris X-33, GS115, KM71H and SMD1168 (Invitrogen). Preferred strains were X-33 and KM71H. Transformation was aimed at stably integrating expression constructs into the genome of the host organism. Initially, 5 ml YPD medium (YPD=yeast peptone dextrose; Invitrogen) was inoculated with a P. pastoris colony and pre-cultured on a shaker overnight at 30° C. To prepare transformation-competent cells, 100 µl of the pre-culture were added as inoculum to 200 ml of fresh YPD medium and grown until an $OD_{600nm}$ of between 1.3 and 1.5 was reached. The cells were centrifuged at 1,500×g for 5 min and resuspended in 200 ml ice cold (0° C.) sterile water. The cells were centrifuged again at 1,500×g for 5 min and resuspended in 100 ml ice cold sterile water. The cells were centrifuged one more time at 1,500×g for 5 min and resuspended in 10 ml ice cold 1 M sorbitol (ICN). The cells prepared in this way were kept on ice and used for transformation immediately.

The pPICZαA-derived pTrySer172Ala expression vectors to be used for transformation were linearised using the Sac I restriction endonuclease (Roche Diagnostics GmbH), precipitated and resuspended in water. Transformation was accomplished by electroporation using a "Gene Pulser II™" (BioRad). For a transformation setting, 80 µl P. pastoris cells in 1 M sorbitol solution were mixed gently with 1 µg of linearised expression vector DNA and transferred into an ice cold cuvette which was then kept on ice for 5 min. Subsequently, the cuvette was transferred into the Gene Pulser. Electroporation parameters were 1 kV, 1 kΩ and 25 µF. Following electroporation, 1 ml 1 M sorbitol solution was added to the cell suspension was subsequently plated onto YPDS plates (YPDS=yeast peptone dextrose sorbitol; Invitrogen) containing 100 µg/ml Zeocin™ (Invitrogen), with 100-150 µl of cell suspension being spread on a single plate. YPDS plates were incubated at 30° C. for 2-4 days. Yeast clones were transferred onto gridded minimal dextrose plates. Colonies from these plates were picked and separately resuspended in sterile water. The cells were digested with 17.5 units of lyticase (Roche Diagnostics GmbH) for 1 h at 30° C. and afterwards frozen for 10 min at −80° C. By means of PCR, the presence of the expression cassettes of the respective pPICZαA-derived pTrySer172Ala expression vector was verified. The term "expression cassette" denotes a nucleotide sequence encoding the variant recombinant porcine pancreatic trypsin pre-protein, operably linked to the AOX1 promoter and the AOX1 terminator, whereby the expression cassette is derived from the respective pPICZαA-vector used for transformation. As for vectors containing an expression cassette, the terms "vector" and "expression vector" are synonyms.

Positive clones, i.e. clones that were tested positively for the presence of complete expression cassettes stably integrated into the genome were used for further characterisation of variant recombinant porcine pancreatic trypsin expression.

Additionally, control transformations were made with the recipient *Pichia pastoris* KM71H strain using the original pPICZαA vector. Positive clones were obtained and verified in a similar fashion.

Example 5

Expression and Secretion of Variant Recombinant Porcine Pancreatic Trypsinogen

A set of positive clones (20-30) transformed with a pPIC-ZαA-pTrySer172Ala expression vector were grown as shaking cultures overnight, each in 3 ml BMGY medium (BMGY=buffered glycerol-complex medium; Invitrogen). Afterwards, the $OD_{600nm}$ values of the cultures were determined before they were passaged into shaking flasks, each containing 10 ml BMMY medium (Invitrogen) at pH 3. Pre-cultures were used as inoculum to result each in an $OD_{600nm}$ of 1. The cultures were kept on a shaker at 30° C. In parallel, positive control clones were cultured under the same conditions.

BMMY (BMMY=buffered methanol-complex medium;) medium comprises methanol (Mallinckrodt Baker B. V.) which is an inductor of the AOX-1 promoter that controls transcription of the nucleotide sequence encoding the variant recombinant porcine pancreatic trypsinogen.

Samples of 500 µl were taken from the shaking flask in 24 h intervals over a total time of 72 h. When a sample aliquot was removed, the culture was also fed with 0.5% methanol. Samples of the supernatant growth medium were tested for trypsin enzymatic activity.

Example 6

Analysis of Expression of Variant Porcine Pancreatic Trypsin

Of the sample aliquots obtained as described in Example 5 firstly the $OD_{600nm}$ was determined. Subsequently the cells were pelleted by centrifugation and the supernatant was saved. trypsin activity was measured in the undiluted supernatant as well as in a 1:10 dilution.

While control clones transformed with the pPICZαA vector did not lead to any measurable trypsin activity in the medium, *Pichia* strains transformed with pPICZαA-pTrySer172Ala expression vectors showed trypsin activity due to the respective variant of recombinant porcine pancreatic trypsin secreted into the growth medium, i.e. the culture medium. It could therefore be concluded that expression of a recombinant pre-protein which in this case comprises the α-factor signal peptide from *Saccharomyces cerevisiae* enables secretion of an active enzyme with proteolytic activity.

Example 7

Increasing Expression Yield by Multiple Transformation and Increased Zeocin™ Concentration The yeast clones transformed with the pPICZαA- and pPICZA-derived pDNM expression vectors that were found to produce the highest trypsin activities in supernatant media were subjected to repeated electroporation using the same expression vector as previously. Conditions for electroporation were as described in Example 4 with the exception that YPDS plates contained Zeocin™ at increased concentrations, that is between 1,000 and 2,000 µg/ml. The concentration of the antibiotic was increased in order to select for transformants having incorporated into their genome multiple copies of the respective expression vector. Yeast clones with increased resistance to the antibiotic were transferred onto gridded minimal dextrose plates. As already described in Example 5, pre-cultures were made from individual yeast clones and expression was measured by determining the trypsin enzymatic activity secreted into the growth medium as described in Example 6. Individual clones were found that produced an increased amount of trypsin activity. On the average, trypsin activity measured in the supernatant of *Pichia* strains repeatedly transformed with the respective pPICZαA-pTry-Ser172Ala expression vector was between twice to three times as high compared to the respective precursor strains that had undergone only a single transformation.

Example 8

Purification of the Variant of Porcine Pancreatic Trypsinogen from Liquid Culture Supernatant and Activation to Form the Trypsin Variant The entire fermentation broth was diluted in a ratio of about 1:2 to 1:4 with ammonium acetate buffer (5-20 mM) containing 5-30 mM calcium chloride, pH 3.5. The trypsinogen variant was purified by means of expanded bed chromatography (McCornick (1993); EP 0 699 687) using a cation exchanger (e.g. Streamline® SP, XL). Chromatography was carried out without prior separation of the yeast cells. Further purification was done using a packed bed column (e.g. SP-Sepharose® XL, ff). Autocatalytic activation was started by rebuffering the pH to 7-8 in the presence of 20 mM $CaCl_2$. Activation was terminated by changing the pH back into the range of 2-4. Purified trypsin was stored at pH 1.5-3 in order to avoid autoproteolysis.

Example 9

Assay to Determine the Specific Trypsin Activity of Purified Variant Recombinant Porcine Pancreatic Trypsin The activity of trypsin was determined using Chromozym TRY (Roche Diagnostics GmbH) in 100 mM Tris pH 8.0, 20 mM $CaCl_2$ at 25° C. Photometric measurement was carried out at 405 nm. To discriminate between the substrate specificity arginine versus lysine the Chromozym TH (contain arginine/Roche Diagnostics GmbH) and Chromozym PL (contain lysine/Roche Diagnostics GmbH) were used.

Example 10

Cleavage of Pre-Pro-Human Insulin

All experiments were conducted at 8° C. and a pH value of 8.3 (buffered solution or controlled by NaOH dosage) and were performed on the 20 mL to the 3.5 L scale. In some experiments, the pre-pro-insulin was also cleaved using native, recombinant porcine trypsin in order to directly compare both enzymes.

The PPI solution was filled in an appropriate thermostated reaction vessel and the reaction was started by addition of the enzyme preparation. Samples were taken after definite time intervals; the enzymatic reaction was immediately stopped by acidifying the sample solution by a 1 N or 2 N HCl solution. The concentration of the respective products were determined by HPLC.

Table 1 depicts exemplary results of one experiment.

TABLE 1

Results of pre-pre-insulin (human insulin) cleavage reaction using native, recombinant porcine trypsin and the S172A Trypsin variant (equal U/g PPI used).

| scale | Trypsin | Σ pre-Arg-Ins [area %] | Σ Arg-Ins [area %] | des-Thr [area %] | Σ A0 compounds [area %] | Yield (external standard) [%] |
|---|---|---|---|---|---|---|
| 3.5 L | native | 1.4 | 68.8 | 7.2 | 10.7 | 84.2 |
|  | S172A | 0.9 | 82.5 | 3.3 | 4.1 | 96.5 |

As can be seen from Table 1, the use of the S172A Trypsin variant decreases the formation of the undesired by-products des-Thr and A0-compounds and consequently increases the amount of valuable Arg-insulins (Arg-Ins) and the respective cleavage yield.

Figure 5:
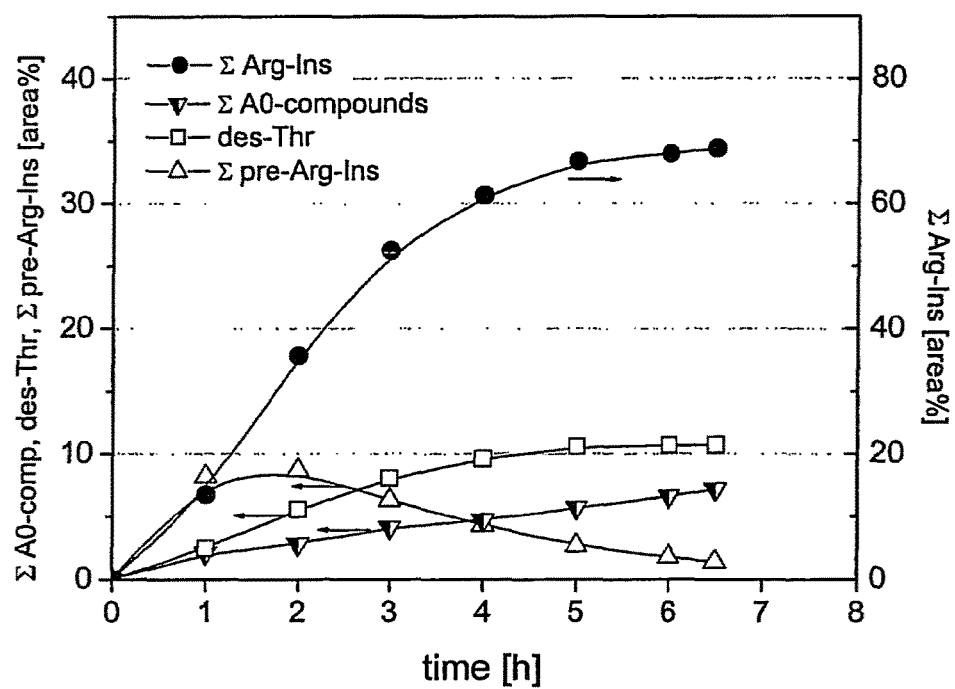
FIG. 5: Pre-pro-insulin (human insulin) cleavage with native, recombinant porcine trypsin (Example 10, Table 1) is shown.
Figure 6:
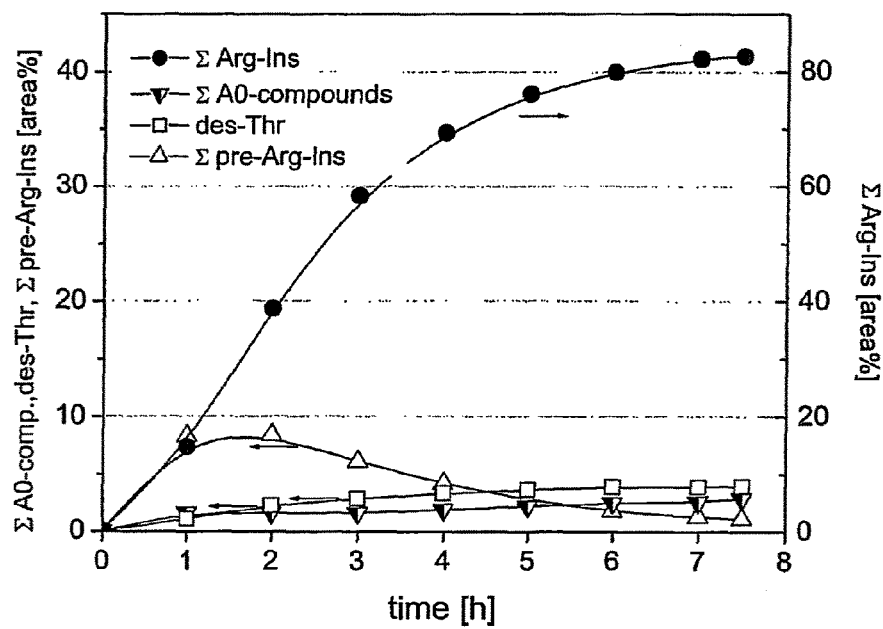
FIG. 6: Pre-pro-insulin (human insulin) cleavage with S172A variant porcine trypsin (Example 10, Table 1) is shown.

FIG. 5 shows conversion of the pre-pro-insulin with native, recombinant porcine trypsin, FIG. 6 shows the conversion of PPI with the S172A variant trypsin.

Example 11

Cleavage of Pre-Pro-Insulin Glargine

Experimental conditions from example 10 were used. Pre-pro-insulin was also cleaved using native, recombinant porcine trypsin in order to directly compare both enzymes.

HPLC method: as described.

Table 2 depicts exemplary results of the performed experiments. The values presented mark the point of maximum product formation.

TABLE 2

Results of pre-pre-insulin (insulin glargine) cleavage reaction using native, recombinant trypsin and the S172A variant (200 U/g PPI used).

| scale | Trypsin | pre-Insulin glargine [area %] | Insulin glargine [area %] | des-Thr [area %] | Σ A0 compounds [area %] | Yield (external standard) [%] |
|---|---|---|---|---|---|---|
| 1 L | native | 0.5 | 51.1 | 5.6 | 10.9 | 58.1 |
|  | S172A | 0.4 | 55.5 | 2.6 | 5.1 | 62.9 |

As can be seen from Table 2, the use of the S172A Trypsin variant decreases the formation of the undesired by-products des-Thr and A0-compounds and consequently increases the amount of insuline glargine.

Example 12

Cleavage of Pre-Pro-Insulin Glulisine

Experimental conditions from example 10 were used. Pre-pro-insulin was also cleaved using native, recombinant porcine trypsin in order to directly compare both enzymes. Table 3 depicts exemplary results of the experiments. The values presented mark the point of maximum product formation.

TABLE 3

Results of pre-pre-insulin (insulin glulisine) cleavage reaction using native, recombinant trypsin and the S172A Trypsin variant.

| scale | Trypsin | Trypsin amount [U/g of PPI] | Arg-insulin-glulisine [area %] | A0-Arg-insulin glulisine [area %] | Yield (external standard) [%] |
|---|---|---|---|---|---|
| 1 L | native | 250 | 35.8 | 4.7 | 91.6 |
|  | S172A | 250 | 39.2 | 1.2 | 100.0 |

As can be seen from Table 3, the use of the S172A Trypsin variant decreases the formation of the undesired A0-compound and consequently increases the amount of insuline glulisine.

The invention claimed is:

1. A method of preparing insulin, an insulin analog or an insulin derivative, comprising the steps of:
   (a) cleaving a pre-pro-insulin, a pre-pro-insulin analog or a pre-pro-insulin derivative with Ser172Ala porcine trypsin to obtain cleavage products, wherein said Ser172Ala porcine trypsin is activated from the polypeptide as set forth in SEQ ID NO: 3,
   (b) separating the cleavage products of (a), and
      (i) if one or more of the cleavage products is an insulin analog or an insulin derivative, performing a further step comprising: obtaining the insulin analog or the insulin derivative, or
      (ii) if one or more of the cleavage products is a precursor of: insulin, an insulin analog or an insulin derivative, performing further steps comprising:
         (1) processing the cleavage products to obtain insulin, the insulin analog or the insulin derivative,
         (2) separating the insulin, the insulin analog or the insulin derivative, and
         (3) obtaining the insulin, the insulin analog or the insulin derivative
   wherein the insulin, the insulin analog or the insulin derivative is prepared.

2. The method according to claim 1, wherein the insulin is human insulin.

3. The method according to claim 1, wherein the insulin analog is selected from the group consisting of Lys$^{B28}$Pro$^{B29}$ human insulin, B28 Asp human insulin, human insulin having proline in position B28 substituted by Asp, Lys, Leu, Val or Ala with or without Lys in position B29 Lys substituted by Pro; AlaB26 human insulin; des(B28-B30) human insulin; des(B27) human insulin and des(B30) human insulin.

4. The method according to claim 1, wherein the insulin analog is insulin glulisine.

5. The method according to claim 1, wherein the insulin analog is insulin glargine.

6. The method according to claim 1, wherein the insulin derivative is selected from the group consisting of B29-N-myristoyl-des(B30) human insulin, B29-N-palmitoyl-des(B30) human insulin, B29-N-myristoyl human insulin, B29-N-palmitoyl human insulin, B28-N-myristoyl Lys$^{B28}$pro$^{B29}$ human insulin, B28-N-palmitoyl-Lys$^{B28}$pro$^{B29}$ human insulin, B30-N-myristoyl-Thr$^{B29}$Lys$^{B30}$ human insulin, B30-N-palmitoyl-Thr$^{B29}$Lys$^{B30}$ human insulin, B29-N—(N-palmitoyl-Y-glutamyl)-des(B30) human insulin, B29-N—(N-lithocholyl-Y-glutamyl)-des(B30) human insulin, B29-N-(ω-carboxyheptadecanoyl)-des(B30) human insulin and B29-N-(ω-carboxyheptadecanoyl) human insulin.

7. The method according to claim 1, wherein the processing step of (ii)(1) comprises cleavage of said cleavage products with Carboxypeptidase B.

8. The method according to claim 1, wherein the cleavage with Ser172Ala porcine trypsin is performed at a pH-value in the range of 7.5 to 9.5, a temperature between 1° C. and 30° C., and the enzymatic reaction is stopped by acidifying the sample.

9. The method according to claim 8, wherein the cleavage is performed at a pH-value of 8.3, a temperature between 8° C. and 12° C., and the acidification is brought about by adding 1N or 2N HCl solution.

10. An isolated Ser172Ala porcine trypsin, activated from the polypeptide as set forth in SEQ ID NO: 3.

11. An isolated polypeptide comprising the amino acid sequence as set forth in SEQ ID NO: 3.

* * * * *

SEQUENCE LISTING

<160> NUMBER OF SEQ ID NOS: 11

<210> SEQ ID NO 1
<211> LENGTH: 223
<212> TYPE: PRT
<213> ORGANISM: Artificial Sequence
<220> FEATURE:
<223> OTHER INFORMATION: Description of mature sequence: sequence of the
      wild-type porcine pancreatic Trypsin without
      signal peptide and Propeptide
<220> FEATURE:
<223> OTHER INFORMATION: Description of Artificial Sequence: primer

<400> SEQUENCE: 1

Ile Val Gly Gly Tyr Thr Cys Ala Ala Asn Ser Ile Pro Tyr Gln Val
 1               5                  10                  15

Ser Leu Asn Ser Gly Ser His Phe Cys Gly Gly Ser Leu Ile Asn Ser
             20                  25                  30

Gln Trp Val Val Ser Ala Ala His Cys Tyr Lys Ser Arg Ile Gln Val
         35                  40                  45

Arg Leu Gly Glu His Asn Ile Asp Val Leu Glu Gly Asn Glu Gln Phe
 50                  55                  60

Ile Asn Ala Ala Lys Ile Ile Thr His Pro Asn Phe Asn Gly Asn Thr
65                  70                  75                  80

Leu Asp Asn Asp Ile Met Leu Ile Lys Leu Ser Ser Pro Ala Thr Leu
                 85                  90                  95

Asn Ser Arg Val Ala Thr Val Ser Leu Pro Arg Ser Cys Ala Ala Ala
            100                 105                 110

Gly Thr Glu Cys Leu Ile Ser Gly Trp Gly Asn Thr Lys Ser Ser Gly
        115                 120                 125

Ser Ser Tyr Pro Ser Leu Leu Gln Cys Leu Lys Ala Pro Val Leu Ser
    130                 135                 140

Asp Ser Ser Cys Lys Ser Ser Tyr Pro Gly Gln Ile Thr Gly Asn Met
145                 150                 155                 160

Ile Cys Val Gly Phe Leu Glu Gly Gly Lys Asp Ser Cys Gln Gly Asp
                165                 170                 175

Ser Gly Gly Pro Val Val Cys Asn Gly Gln Leu Gln Gly Ile Val Ser
            180                 185                 190

Trp Gly Tyr Gly Cys Ala Gln Lys Asn Lys Pro Gly Val Tyr Thr Lys
        195                 200                 205

Val Cys Asn Tyr Val Asn Trp Ile Gln Gln Thr Ile Ala Ala Asn
    210                 215                 220

<210> SEQ ID NO 2
<211> LENGTH: 687
<212> TYPE: DNA
<213> ORGANISM: Artificial Sequence
<220> FEATURE:
<223> OTHER INFORMATION: Description of Artificial Sequence: sequence
      encoding the porcine pancreatic Trypsinogen
      without signal peptide and the part of the
      propeptide encoding the enterokinase cleavage site

<400> SEQUENCE: 2
gatgatgatg ataaaattgt tggtggttat acttgtgctg ctaattctat tccatatcaa      60
gtttctttaa attctggttc tcattttgt ggtggttctt tgattaattc tcaatgggtt     120
gtttctgctg ctcattgtta caaatcaaga atccaagtta gattgggtga acataatatt    180
gatgttttgg aaggtaatga acaatttatt aatgctgcta aaattattac tcatccaaat    240

-continued

```
tttaatggta atactttgga taatgatatt atgttgatta aattgtcttc tccagctact    300
ttaaattcaa gagttgctac tgtttctttg ccaagatctt gtgctgctgc tggtactgaa    360
tgtttgattt ctggttgggg taatactaaa tcttctggtt cttcttatcc atctttgttg    420
caatgtttga aagctccagt tttgtctgat tcttcttgta aatcttctta cccaggtcaa    480
attactggta atatgatttg tgttggtttt tggaaggtg gtaaagattc ttgtcaaggt     540
gattctggtg gtccagttgt tgtaatggt caattgcaag gtattgtttc ttggggttat    600
ggttgtgctc aaaaaaataa accaggtgtt tacactaaag tttgtaatta tgttaattgg    660
attcaacaaa ctattgctgc taattag                                        687
```

<210> SEQ ID NO 3
<211> LENGTH: 223
<212> TYPE: PRT
<213> ORGANISM: Artificial Sequence
<220> FEATURE:
<223> OTHER INFORMATION: Description of Artificial Sequence: amino acid
      sequence of the variant porcine pancreatic Trypsin
<220> FEATURE:
<221> NAME/KEY: PEPTIDE
<222> LOCATION: (1)..(223)

<400> SEQUENCE: 3

Ile Val Gly Gly Tyr Thr Cys Ala Ala Asn Ser Ile Pro Tyr Gln Val
 1               5                  10                  15

Ser Leu Asn Ser Gly Ser His Phe Cys Gly Gly Ser Leu Ile Asn Ser
             20                  25                  30

Gln Trp Val Val Ser Ala Ala His Cys Tyr Lys Ser Arg Ile Gln Val
         35                  40                  45

Arg Leu Gly Glu His Asn Ile Asp Val Leu Glu Gly Asn Glu Gln Phe
     50                  55                  60

Ile Asn Ala Ala Lys Ile Ile Thr His Pro Asn Phe Asn Gly Asn Thr
 65                  70                  75                  80

Leu Asp Asn Asp Ile Met Leu Ile Lys Leu Ser Ser Pro Ala Thr Leu
                 85                  90                  95

Asn Ser Arg Val Ala Thr Val Ser Leu Pro Arg Ser Cys Ala Ala Ala
            100                 105                 110

Gly Thr Glu Cys Leu Ile Ser Gly Trp Gly Asn Thr Lys Ser Ser Gly
        115                 120                 125

Ser Ser Tyr Pro Ser Leu Leu Gln Cys Leu Lys Ala Pro Val Leu Ser
    130                 135                 140

Asp Ser Ser Cys Lys Ser Ser Tyr Pro Gly Gln Ile Thr Gly Asn Met
145                 150                 155                 160

Ile Cys Val Gly Phe Leu Glu Gly Gly Lys Asp Ala Cys Gln Gly Asp
                165                 170                 175

Ser Gly Gly Pro Val Val Cys Asn Gly Gln Leu Gln Gly Ile Val Ser
            180                 185                 190

Trp Gly Tyr Gly Cys Ala Gln Lys Asn Lys Pro Gly Val Tyr Thr Lys
        195                 200                 205

Val Cys Asn Tyr Val Asn Trp Ile Gln Gln Thr Ile Ala Ala Asn
    210                 215                 220

<210> SEQ ID NO 4
<211> LENGTH: 687
<212> TYPE: DNA
<213> ORGANISM: Artificial Sequence
<220> FEATURE:
<223> OTHER INFORMATION: Description of Artificial Sequence: sequence encoding the variant of porcine pancreatic
Trypsinogen without signal peptide and the part of
the propeptide encoding the enterokinase cleavage
site

<400> SEQUENCE: 4

| gatgatgatg ataaaattgt tggtggttat acttgtgctg ctaattctat tccatatcaa | 60 |
| gtttctttaa attctggttc tcattttgt ggtggttctt tgattaattc tcaatgggtt | 120 |
| gtttctgctg ctcattgtta caaatcaaga atccaagtta gattgggtga acataatatt | 180 |
| gatgttttgg aaggtaatga acaatttatt aatgctgcta aaattattac tcatccaaat | 240 |
| tttaatggta atactttgga taatgatatt atgttgatta aattgtcttc tccagctact | 300 |
| ttaaattcaa gagttgctac tgtttctttg ccaagatctt gtgctgctgc tggtactgaa | 360 |
| tgtttgattt ctggttgggg taatactaaa tcttctggtt cttcttatcc atctttgttg | 420 |
| caatgtttga agctccagt tttgtctgat tcttcttgta atcttcttac cccaggtcaa | 480 |
| attactggta atatgatttg tgttggtttt ttggaaggtg gtaaagatgc ttgtcaaggt | 540 |
| gattctggtg gtccagttgt ttgtaatggt caattgcaag gtattgtttc ttggggttat | 600 |
| ggttgtgctc aaaaaaataa accaggtgtt tacactaaag tttgtaatta tgttaattgg | 660 |
| attcaacaaa ctattgctgc taattag | 687 |

<210> SEQ ID NO 5
<211> LENGTH: 247
<212> TYPE: PRT
<213> ORGANISM: Artificial Sequence
<220> FEATURE:
<223> OTHER INFORMATION: Amino acid sequence of the mature porcine
      Pre-Trypsinogen
<220> FEATURE:
<221> NAME/KEY: PEPTIDE
<222> LOCATION: (1)..(16)
<223> OTHER INFORMATION: amino acid sequence of the signal peptide
<220> FEATURE:
<221> NAME/KEY: PEPTIDE
<222> LOCATION: (17)..(247)
<223> OTHER INFORMATION: amino acid sequence of porcine Trypsinogen
<220> FEATURE:
<223> OTHER INFORMATION: Description of Artificial Sequence: primer
<300> PUBLICATION INFORMATION:

<400> SEQUENCE: 5

Ile Pro Asn Thr Phe Val Leu Leu Ala Leu Leu Gly Ala Ala Val Ala
 1               5                  10                  15

Phe Pro Thr Asp Asp Asp Asp Lys Ile Val Gly Gly Tyr Thr Cys Ala
                20                  25                  30

Ala Asn Ser Ile Pro Tyr Gln Val Ser Leu Asn Ser Gly Ser His Phe
            35                  40                  45

Cys Gly Gly Ser Leu Ile Asn Ser Gln Trp Val Val Ser Ala Ala His
        50                  55                  60

Cys Tyr Lys Ser Arg Ile Gln Val Arg Leu Gly Glu His Asn Ile Asp
    65                  70                  75                  80

Val Leu Glu Gly Asn Glu Gln Phe Ile Asn Ala Ala Lys Ile Ile Thr
                85                  90                  95

His Pro Asn Phe Asn Gly Asn Thr Leu Asp Asn Asp Ile Met Leu Ile
            100                 105                 110

Lys Leu Ser Ser Pro Ala Thr Leu Asn Ser Arg Val Ala Thr Val Ser
        115                 120                 125

Leu Pro Arg Ser Cys Ala Ala Ala Gly Thr Glu Cys Leu Ile Ser Gly
    130                 135                 140

```
Trp Gly Asn Thr Lys Ser Ser Gly Ser Ser Tyr Pro Ser Leu Leu Gln
145                 150                 155                 160

Cys Leu Lys Ala Pro Val Leu Ser Asp Ser Ser Cys Lys Ser Ser Tyr
                165                 170                 175

Pro Gly Gln Ile Thr Gly Asn Met Ile Cys Val Gly Phe Leu Glu Gly
            180                 185                 190

Gly Lys Asp Ser Cys Gln Gly Asp Ser Gly Gly Pro Val Val Cys Asn
        195                 200                 205

Gly Gln Leu Gln Gly Ile Val Ser Trp Gly Tyr Gly Cys Ala Gln Lys
    210                 215                 220

Asn Lys Pro Gly Val Tyr Thr Lys Val Cys Asn Tyr Val Asn Trp Ile
225                 230                 235                 240

Gln Gln Thr Ile Ala Ala Asn
                245

<210> SEQ ID NO 6
<211> LENGTH: 960
<212> TYPE: DNA
<213> ORGANISM: Pichia pastoris
<220> FEATURE:
<223> OTHER INFORMATION: Nucleotide sequence of the variant of porcine
      pancreatic pre-Trypsinogen
<220> FEATURE:
<221> NAME/KEY: unsure
<222> LOCATION: (1)..(267)
<223> OTHER INFORMATION: nucleotide sequence encoding the signal peptide
<220> FEATURE:
<221> NAME/KEY: unsure
<222> LOCATION: (268)..(960)
<223> OTHER INFORMATION: encoding the variant porcine pancreatic
      Trypsinogen

<400> SEQUENCE: 6
atgagatttc cttcaattt tactgctgtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180 aacggttat tgtttataaa tactactatt gccagcattg ctgctaaaga agaagggta     240 tctctcgaga aaagagaggc tgaagctgaa ttcgatgatg atgataaaat tgttggtggt     300
tatacttgtg ctgctaattc tattccatat caagtttctt taaattctgg ttctcatttt     360
tgtggtggtt ctttgattaa ttctcaatgg gttgtttctg ctgctcattg ttacaaatca     420
agaatccaag ttagattggg tgaacataat attgatgttt ggaaggtaa tgaacaattt     480 attaatgctg ctaaaattat tactcatcca aattttaatg gtaatacttt ggataatgat     540
attatgttga ttaaattgtc ttctccagct actttaaatt caagagttgc tactgtttct     600
ttgccaagat cttgtgctgc tgctggtact gaatgtttga tttctggttg gggtaatact     660
aaatcttctg gttcttctta tccatctttg ttgcaatgtt tgaaagctcc agtttttgtct    720 gattcttctt gtaaatcttc ttacccaggt caaattactg gtaatatgat ttgtgttggt     780
tttttggaag gtggtaaaga tgcttgtcaa ggtgattctg gtggtccagt tgtttgtaat     840
ggtcaattgc aaggtattgt ttcttggggt tatggttgtg ctcaaaaaaa taaaccaggt     900
gtttacacta agtttgtaa ttatgttaat tggattcaac aaactattgc tgctaattaa     960

<210> SEQ ID NO 7
<211> LENGTH: 938
<212> TYPE: DNA
<213> ORGANISM: Pichia pastoris
<220> FEATURE:
<223> OTHER INFORMATION: Nucleotice sequence of the Pichia pastoris AOX1
``` promoter

<400> SEQUENCE: 7

```
agatctaaca tccaaagacg aaaggttgaa tgaaaccttt ttgccatccg acatccacag    60
gtccattctc acacataagt gccaaacgca acaggagggg atacactagc agcagaccgt   120
tgcaaacgca ggacctccac tcctcttctc ctcaacaccc acttttgcca tcgaaaaacc   180
agcccagtta ttgggcttga ttggagctcg ctcattccaa ttccttctat taggctacta   240
acaccatgac tttattagcc tgtctatcct ggccccnctg gcgaggttca tgtttgttta   300
tttccgaatg caacaagctc cgcattacac ccgaacatca ctccagatga gggctttctg   360
agtgtggggt caaatagttt catgttcccc aaatggccca aaactgacag tttaaacgct   420
gtcttggaac ctaatatgac aaaagcgtga tctcatccaa gatgaactaa gtttggttcg   480
ttgaaatgct aacggccagt tggtcaaaaa gaaacttcca aaagtcggca taccgtttgt   540
cttgtttggt attgattgac gaatgctcaa aaataatctc attaatgctt agcgcagtct   600
ctctatcgct tctgaacccc ggtgcacctg tgccgaaacg caaatgggga aacacccgct   660
ttttggatga ttatgcattg tctccacatt gtatgcttcc aagattctgg tgggaatact   720
gctgatagcc taacgttcat gatcaaaatt taactgttct aaccnctact tgacagcaat   780
atataaacag aaggaagctg ccctgtctta aacctttttt tttatcatca ttattagctt   840
actttcataa ttgcgactgg ttccaattga caagcttttg attttaacga cttttaacga   900
caacttgaga agatcaaaaa acaactaatt attcgaaa                           938
```

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: primer 5'
-Trypsin

<400> SEQUENCE: 8

```
gctgaagctg aattcgatga tgatg                                          25
```

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: primer
3'-Trypsin

<400> SEQUENCE: 9

```
gttttttgttc tagactaatt agcagc                                        26
```

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: primer
5'-Try-Ser172Ala

<400> SEQUENCE: 10

```
ggtggtaaag atgcttgtca aggtg                                          25
```

<210> SEQ ID NO 11
<211> LENGTH: 25
<212> TYPE: DNA
<213> ORGANISM: Artificial Sequence -continued

```
<220> FEATURE:
<223> OTHER INFORMATION: Description of Artificial Sequence: primer
      3'-Try-Ser172Ala

<400> SEQUENCE: 11
caccttgaca ggcatcttta ccacc                                         25
```